United States Patent
Yvin et al.

(10) Patent No.: US 6,632,940 B1
(45) Date of Patent: Oct. 14, 2003

(54) METHOD FOR LAMINARIBIOSE SYNTHESIS

(75) Inventors: Jean-Claude Yvin, Saint Malo (FR); Frank Jamois, Rennes (FR); Vincent Ferrieres, Rennes (FR); Daniel Plusquellec, Noyal Chatillon sur Seiche (FR)

(73) Assignee: Laboratoires Goemar, Saint Malo (FR)

( * ) Notice: Subject to any disclaimer, the term of this patent is extended or adjusted under 35 U.S.C. 154(b) by 0 days.

(21) Appl. No.: 09/673,295

(22) PCT Filed: Apr. 13, 1999

(86) PCT No.: PCT/FR99/00857

§ 371 (c)(1),
(2), (4) Date: Oct. 13, 2000

(87) PCT Pub. No.: WO99/52920

PCT Pub. Date: Oct. 21, 1999

(30) Foreign Application Priority Data

Apr. 14, 1998 (FR) .............................. 98 04610

(51) Int. Cl.$^7$ .............................................. C13K 5/00
(52) U.S. Cl. .................. 536/123.13; 536/107; 536/108; 536/115; 536/116; 536/123.1; 514/35; 514/53
(58) Field of Search ...................... 514/53, 35; 536/107, 536/108, 123.13, 115, 116, 123.1

(56) References Cited

PUBLICATIONS

Fukase et al., "A novel method for activation of thioglycosides, combination of N–bromosuccinimide and triflic acid salts", Abstract to Tetrahedron Lett. 34(13), pp. 2187–2190, 1993.*

Durette, P. L. et al., "Conformational Analysis of Sugars and their Derivatives", In Advances in Carbohydrate Chemistry and Biochemistry, vol. 26, 1971, pp. 49, 55–60.*

Horton, D. et al., "Conformational Properties of Sugars and their Derivatives", In Annals of the New York Academy of Sciences, vol. 222, 1973, pp. 884–893.*

Takeo, K. "Synthesis of Benzyl α– and β–Sophorosides, and of Benzyl α–laminarabioside," *Carbohydrate Research*, vol. 86, No. 1 (1980): pp. 151–157. XP–002090785.

Takeo, K. "A Convenient Synthesis of Laminarabiose and Some of its Glycosides," *Carbohydrate Research*, vol. 77 (1979): pp. 245–251. XP–002090786.

Forzato, C. et al. "Baker's Yeast Reduction of 4–hetero–2–(2–nitroethyl)cyclohexanones," *Tetrahedron: Asymmetry*, vol. 8, No. 11 (1997): pp. 1811–1820. XP–002090787.

Bachli et al. "The Synthesis of Laminaribiose (3– α–D–Glucosyl D–Glucose) and Proof of its Identity with Laminaribiose isolated from Laminarian," *J. Chem. Soc.*, (1952): pp. 1243–1246.

Kochetkov et al. "Modifications of the Orthoester Method of Glycosylation," *Carbohydr. Res.*, vol. 16 (1971): pp. 17–27.

Villa et al. "A Method for preparing laminaribiose by using yeast endo–(1→3)β–D–glucanase," *Carbohydrate Research*, vol. 74 (1979): pp. 369–370.

Kusama et al. "Enzymatic Preparation of Crystalline Laminaribiose from Curdlan," *Agric. Biol. Chem.*, vol. 48, No. 6 (1984): pp. 1433–1440.

Wang et al. "Peracetylated laminaribiose: preparation by specific degradation of curdlan and its chemical conversion into N–acetylhyalobiuronic acid," *Carbohydrate Research*, vol. 219 (1991): pp. 133–148.

Moreau et al. "Design and chemoenzymatic synethesis of thiooligosaccharide inhibitors of 1,3: 1,4–β–D–glucanases," *Bioorganic & Medicinal Chemistry*, vol. 4, No. 11 (1996): pp. 1849–1855.

Koenigs et al. "Ueber einige Derivate des Traubenzuckers und der Galactose"*Berichete d. D. chem.. Gesellschaft*, Jahrg. XXXIV: pp. 957–981.

* cited by examiner

*Primary Examiner*—Dwayne C. Jones
(74) *Attorney, Agent, or Firm*—Merchant & Gould P.C.

(57) ABSTRACT

The invention concerns a method for preparing Laminaribiose comprising a step for glycoside binding between a donor and an acceptor of glycosyl. The invention is characterized in that the glycosyl donor is in pyranose form and corresponds to formula (II); the glycosyl acceptor is in furanose form and corresponds to formula (III); said binding step is performed in solution in an anhydrous organic solvent, at a temperature ranging between –80° C. and 40° C., for a time interval ranging between 1 minute and 8 hours, in the presence of a suitable promoter.

14 Claims, No Drawings

METHOD FOR LAMINARIBIOSE SYNTHESIS

CROSS-REFERENCE TO RELATED APPLICATIONS

This application is a §371 application of PCT/FR99/00857 filed on Apr. 13, 1999, which claims priority to French application 98/04610 filed on Apr. 14, 1998.

FIELD OF THE INVENTION

The present invention relates to a novel method of chemical preparation of β-D-glucopyranosyl-(1→3)-D-glucopyranose of formula (I), commonly called laminaribiose.

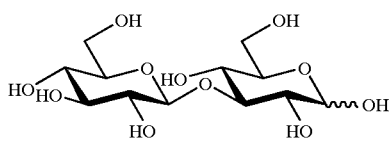

(I)

BACKGROUND OF THE INVENTION

Laminaribiose is a disaccharide which is used notably in the agricultural field and as an antiseptic.

This disaccharide is in general obtained by hydrolysis or by acetolysis of natural polysaccharides of plant origin (see Villa, Phaff, Notario, *Carbohydr. Res.*, 1979, 74, 369; Kusama, Kusakabe, Zama, Murakami, Yasui, *Agric. Biol. Chem.*, 1984, 48, 1433; Wang, Sakairi, Kuzuhara, *Carbohydr. Res.*, 1991, 219, 133; Moreau, Viladot, Samain, Planas, Driguez, *Bioorg. Med. Chem.*, 1996, 4, 1849).

Laminaribiose can also be prepared chemically, notably by methods derived from the Koenigs-Knorr method of O-glycosylation (see Koenigs, Knorr, *Ber. Dtsch. Chem. Ges.*, 1901, 34, 957) which makes use of glycosyl halides as glycosyl donors.

A first method has thus been proposed by Freudenberg and von Oertzen in 1951 (see Freudenberg, von Oertzen, *Justus Liebigs Ann. Chem.*, 1951, 574, 37), and a second method has been described by Bächli and Percival in 1952 (see Bäichli, Percival, *J. Chem. Soc.*, 1952, 1243).

The major drawbacks of these two methods reside in a purification which is difficult to carry out and in an overall yield which is lower that 10%.

A third method has been proposed by Takeo in 1979 (see Takeo, *Carbohydr. Res.*, 1979, 77, 245), but it necessitates several steps of selective protection and deprotection of the hydroxyls of the acceptor used which is in glucopyranose form.

It has also been proposed to form laminaribiose from ortho-esters (see Kochetkov, Bochtov, Sokolovskaya, Snyatkova, *Carbohydr. Res.*, 1971, 16, 17). This method does however prove to be difficult to carry out and enables laminaribiose to be obtained only with an overall yield neighbouring 10%.

Under these circumstances, the aim of the present invention is to provide a novel method of chemical preparation of laminaribiose which has a limited number of steps which are easy to carry out and which enables the product sought after to be obtained in pure form with a high overall yield.

SUMMARY OF THE INVENTION

The solution in accordance with the present invention to solve this technical problem consists of a method of preparing laminaribiose comprising a step of glycosidic coupling between a glycosyl donor and a glycosyl acceptor, characterised in that:

the glycosyl donor is in pyranose form and is of formula (II):

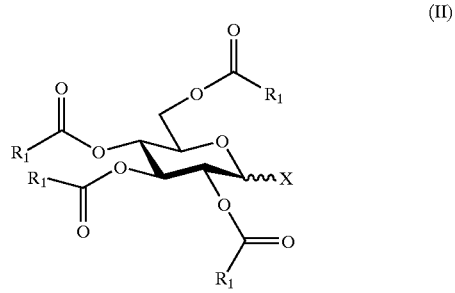

(II)

in which:
R$_1$ represents:
an alkyl or haloalkyl radical having 1 to 6 carbon atoms
an aryl radical which is non-substituted or substituted with one or more groups selected from a halogen atom, an alkoxy radical having 1 to 6 carbon atoms or a nitro group;
X represents an electrophilic leaving group selected from:
a group of formula S(O)$_n$R' in which R' represents an alkyl radical having 1 to 6 carbon atoms, an aryl radical which is non-substituted or substituted with an alkoxy group having 1 to 6 carbon atoms, a nitro or acetamide group, and n is an integer equal to 0 or 1; or
a trichloroacetimidate group;
the glycosyl acceptor is in furanose form and is of formula (III)

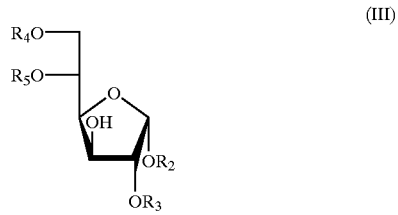

(III)

in which:
R$_2$ and R$_3$ together form a methylidyl, ethylidyl, trichloroethylidyl, isopropylidyl, hexafluoroisopropylidyl, cyclopentylidyl, cyclohexylidyl, cycloheptylidyl, butylidyl, 1-tert-butylethylidyl, 1-phenylethylidyl, benzylidyl, methoxybenzylidyl, or 1-phenylbenzylidyl radical ; and
R$_4$ and R$_5$ together form a methylidyl, ethylidyl, trichloroethylidyl, isopropylidyl, hexafluoroisopropylidyl, cyclopentylidyl, cyclohexylidyl, cycloheptylidyl, butylidyl, 1-tert-butylethylidyl, 1-phenylethylidyl, benzylidyl, methoxybenzylidyl, or 1-phenylbenzylidyl radical, or independently represent a benzyl, acetyl, benzoyl, chlorobenzoyl, methoxybenzoyl, nitrobenzoyl, allyl, chlorobenzyl, methoxybenzyl or nitrobenzyl radical;
said coupling step is carried out in solution in an anhydrous organic solvent, at a temperature between −80°

C. and 40° C., for a period of 1 minute to 8 hours, in the presence of a suitable promoter selected from:
- a source of halonium ions, combined or not with a Lewis acid or a salt of a strong acid, in the case in which X represents an $S(O)_nR'$ group as defined above in which n is equal to 0;
- a Lewis acid combined with an amine, in the case in which X represents an $S(O)_nR'$ group as defined above in which n is equal to 1; or
- a Bronsted acid or a Lewis acid, in the case in which X represents a trichloroacetimidate group ; and the reaction product thus obtained, neutralised and purified, being subjected to a deprotection treatment to give, after purification, laminaribiose.

DETAILED DESCRIPTION OF THE INVENTION

It has been discovered, and this constitutes the basis of the present invention, that it was possible to chemically prepare laminaribiose with a limited number of steps which enable a relatively high overall yield to be obtained, by a judicial choice of the glycosyl donor and of the glycosyl acceptor, as well as of the promoter used during the coupling reaction.

In the description and claims:

<<alkyl radical having 1 to 6 carbon atoms>> is understood as meaning any linear or branched hydrocarbon chain, such as a methyl, ethyl, propyl, isopropyl, butyl, isobutyl, tert-butyl, pentyl, isopentyl, hexyl, or isohexyl radical, for example;

<<haloalkyl radical having 1 to 6 carbon atoms>> is understood as meaning any alkyl radical 1 to 7 hydrogen atoms of which are substituted by 1 to 7 halogen atoms, such as a chloromethyl radical, a bromomethyl radical, a trifluoromethyl radical, a 2,2,2-trifluoroethyl radical, a pentafluoroethyl radical, or a heptafluoropropyl radical, for example;

<<aryl radical>> is understood as meaning an aromatic ring having 5 or 6 carbon atoms or heteroatoms, such as a phenyl, pyridyl, thienyl, furanyl, or pyrimidyl radical, for example.

The glycosyl donor of formula (II) mentioned above as well as the glycosyl acceptor of formula (III) mentioned above can be obtained relatively easily, in one or two steps, from D-glucose.

Advantageously, the glycosyl donor will in general be selected from the compounds of formula (II) mentioned above in which:

$R_1$ represents a radical selected from the group consisting of methyl, chloromethyl, trifluoromethyl, tert-butyl, phenyl, chlorophenyl, methoxyphenyl and nitrophenyl radicals;

X represents a radical selected from the group consisting of thiomethyl, thioethyl, thiopropyl, thiophenyl, thionitrophenyl, and thiopyridyl radicals.

In general, the promoter used during the coupling step mentioned above will be selected from:

N-bromosuccinimide or N-iodosuccinimide, combined or not with a Lewis acid selected from ferric chloride, copper ditriflate, tin ditriflate, boron trifluoride dietherate, tin or zirconium tetrachloride, methyl triflate, trimethyl- (or triethyl-) silyl triflate, silver triflate, cadmium ditriflate, cobalt ditriflate, nickel ditriflate, zinc ditriflate, bismuth tritriflate, iron tritriflate, gallium tritriflate, or with a salt of a strong acid such as tetrabutylammonium triflate, in the case in which X represents an $S(O)_nR'$ group as defined above in which n is equal to O, a Lewis acid selected from triflic anhydride, ferric chloride, copper ditriflate, tin ditriflate, boron trifluoride dietherate, tin or zirconium tetrachloride, methyl triflate, trimethyl- (or triethyl-) silyl triflate, silver triflate, cadmium ditriflate, cobalt ditriflate, nickel ditriflate, zinc ditriflate, bismuth tritriflate, iron tritriflate, gallium tritriflate, combined with an amine particularly such as di-tert-butylmethylpyridine, in the case in which X represents an $S(O)_nR'$ group as defined above in which n is equal to 1, and a Bronsted acid particularly such as triflic acid or para-toluenesulphonic acid or a Lewis acid selected from triflic anhydride, ferric chloride, copper ditriflate, tin ditriflate, boron trifluoride dietherate, tin or zirconium tetrachloride, methyl triflate, trimethyl- (or triethyl-) silyl triflate, silver triflate, cadmium ditriflate, cobalt ditriflate, nickel ditriflate, zinc ditriflate, bismuth tritriflate, iron tritriflate, gallium tritriflate, in the case in which X represents a trichloroacetimidate group.

In a currently preferred embodiment of the method according to the invention:

the glycosyl donor is of formula (II) mentioned above in which:

$R_1$ represents a phenyl radical; and

X represents an $S(O)_nR'$ radical in which n is equal to O and R' represents an ethyl or phenyl radical;

the glycosyl acceptor is of formula (III) mentioned above in which:

$R_2$, $R_3$ and $R_4$, $R_5$ together form a cyclohexylidyl or isopropylidyl radical.

In this particular embodiment, the promoter used during the coupling reaction is constituted of a mixture of N-iodosuccinimide and of tin ditriflate, preferably in proportions between 1:0.5 and 1:0.005.

In general, the coupling step mentioned above is carried out in solution in dichloromethane, 1,2-dichloroethane or toluene, preferably in the presence of molecular sieves, at a temperature between −30° C. and 30° C., for a period of 1 minute to 6 hours, preferably at 10° C. for 30 minutes.

It will be possible for the respective amounts of glycosyl donor, of glycosyl acceptor and of promoter to be determined easily by the person skilled in the art.

In general, the coupling reaction can be carried out by allowing to react:

one equivalent of glycosyl acceptor;

one to two equivalents of glycosyl donor; and one to two equivalents of promoter;

in 5 to 200 equivalents by weight, with respect to the acceptor, of a solvent.

Advantageously, an organic solvent such as dichloromethane, 1,2-dichloroethane or toluene will be used, in the presence of molecular sieves (intended for trapping the acid which can form during the reaction) such as 4 Å molecular sieves for example, used in an amount of 10 to 200 mg/ml of solvent.

The product obtained by the coupling reaction mentioned above is generally neutralised and then purified.

The neutralisation can be carried out by adding an organic base, preferably triethylamine or ethanolamine, or even by adding an inorganic base, preferably sodium or potassium carbonate or hydrogen carbonate, followed by filtering the salt obtained.

The purification can be carried out:

either by chromatography, for example on a silica gel or active charcoal column, or by fractional crystallisation preferably in an organic solvent or a mixture of organic solvents such as ethyl ether, ethyl acetate, cyclohexane or ethanol.

The product of the coupling reaction, neutralised and purified leads, via a deprotection treatment followed by a purification, to laminaribiose.

In general, the deprotection treatment mentioned above comprises two steps, the first consisting of a partial deprotection of the product of the coupling reaction, by cleavage of the acetal groups originating from the glycosyl acceptor.

Within the context of the method in accordance with the present invention, the deprotection treatment comprises:

a) cleaving the acetal groups originating from the glycosyl acceptor by an acidic treatment in an aqueous or hydro-organic medium, or in the presence of an acidic resin;

b) purifying the product thus obtained;

c) transesterifying or hydrolysing the product obtained in step b); and d) purifying the product thus obtained.

The cleavage reaction a) mentioned above will preferably be carried out in an acidic hydro-organic medium, such as in a mixture of equal volumes of trifluoroacetic acid and water for example, at a temperature between 10 and 70° C. for a period of 1 hour to 10 days and in this case, the partially deprotected product obtained will be purified by fractional crystallisation, preferably in methanol, or by chromatography.

It is also possible for acetic acid, oxalic acid, formic acid, sulphuric acid, hydrochloric acid, and phosphoric acid, to be used instead of trifluoroacetic acid.

Within the context of the method in accordance with the present invention, the transesterification step c) mentioned above will be carried out in an alcoholic solvent such as methanol or ethanol in the presence of a catalytic amount of sodium or of sodium or potassium methoxide or ethoxide, for a period of 1 minute to 10 days.

The product of transesterification thus obtained will generally be purified by a method comprising:

d1) neutralising the product obtained in step c);

d2) removing the benzoic ester formed, either by azeotropic evaporation with water, or by extraction with an organic solvent;

d3) concentrating under reduced pressure the residual aqueous phase;

d4) optionally, lyophilising or crystallising the laminaribiose thus obtained in a hydro-alcoholic mixture.

Other characteristics and advantages of the invention will be better understood upon reading the following non-limiting Examples.

EXAMPLE 1

Example of Preparation of a Glycosyl Acceptor

In this example, the glycosyl acceptor, namely 1,2:5,6-di-O-cyclohexylidene-α-D-glucofuranose (compound of formula III in which $R_2$, $R_3$ and $R_4$, $R_5$ represent a cyclohexylidyl radical) was prepared in one single step from D-glucose.

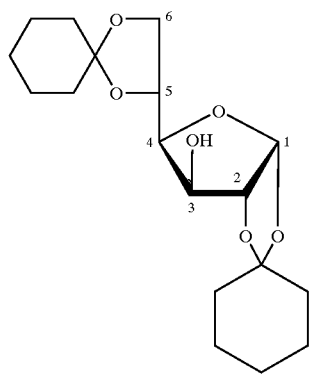

20 ml (375 mmol; 1.03 eq) of concentrated sulphuric acid are added dropwise to 65 g of D-glucose (361 mmol; 1 eq) and 85 ml (820 mmol ; 2.27 eq) of cyclohexanone in 50 ml of 1,4-dioxane (587 mmol; 1.62 eq) at ambient temperature. Once the addition is complete, after 30 minutes, the product precipitates from the reaction medium. The precipitate is broken up, filtered off and washed with water. The crude product is then purified by recrystallisation from cyclohexane to give to 104 grams of 1,2: 5,6-di-O-cyclohexylidene-α-D-glucofuranose.

Yield (%): 85
White solid.
M. Pt. (°C.)=134–136
TLC : $R_f$=0.8 (dichloromethane/methanol (9/1; v/v)).
$^{13}C$ NMR (CDCl$_3$, 101 MHz) δ(ppm): 112.49, 110.32 (C quat.); 104.93 (C1); 84.62 (C2); 81.23 (C4); 75.39 (C3); 73.27 (C5); 67.40 (C6); 36.50, 36.48, 35.69, 34.65, 25.09, 24.94, 24.08, 23.95, 23.82, 23.63, (CH$_2$).
$^1H$ NMR (CDCl$_3$, 400 MHz) δ(ppm): 5.93, (d, 1H, H1, $J_{H1-H2}$=3.6 Hz); 4.50 (d, 1H, H2, $J_{H2-H1}$=3.6 Hz); 4.34–4.30 (m,2H, H3, H5); 4.14 (dd, 1H, H6, $J_{H6-H5}$=6.2 Hz, $J_{H6-H6'}$=8.6 Hz); 4.04 (dd, 1H, H4, $J_{H4-H3}$=2.8 Hz, $J_{H4-H5}$=7.6 Hz); 3.95 (dd, 1H, H6', $J_{H6'-H5}$=5.4 Hz, $J_{H6'-H6}$=8.6 Hz); 1.70–1.36 (m, 20H, CH$_2$).

EXAMPLE 2

Example of Preparation of a Glycosyl Donor

In this example, the glycosyl donor (compound of formula II in which $R_1$ is a phenyl and X is an S(O)$_n$R' group in which n=0 and R' represents an ethyl group) was prepared in two steps.

a) Preparation of 1,2,3,4,6-penta-O-benzoyl-D-glucopyranose

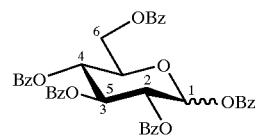

100 g of D-glucose (555 mmol; 1 eq) are dissolved in 2 l of pyridine and the reaction medium is heated under reflux for 1 hour before 387 ml (3,330 mmol; 6 eq) of benzoyl chloride are added thereto in the hot. After addition, the medium is diluted with water, the product precipitates and is filtered off and rinsed with water to neutrality. After drying, it is purified by recrystallisation from ethyl acetate.

Yield (%): 100
White solid.
M. Pt. (°C.)=164–166 (β anomer); 188–191 (α anomer).
TLC: $R_f$=0.3 (petroleum ether/ethyl acetate (8/2; v/v)).

$^{13}$C NMR (CDCl$_3$, 101 MHz) δ(ppm): β anomer: 166.17, 165.74, 165.19, 165.16, 164.66 (C=O); 92.74 (C1); 73.21, 72.85 (C3, C5); 70.87 (C2); 69.08 (C4); 62.71 (C6); α anomer: 166.15, 165.96, 165.42, 165.18, 164.47 (C=O); 90.08 (C1); 70.54, 70.51, 70.45 (C2, C3, C5); 68.83 (C4); 62.49 (C6).

$^1$H NMR (CDCl$_3$, 400 MHz) δ(ppm): 8.20–7.16 (m, 25H, H arom.); β anomer: 6.30 (d, 1H, H1, $J_{H1\text{-}H2}$=8.0 Hz); 6.05 (t, 1H, H3, $J_{H3\text{-}H2}$=$J_{H3\text{-}H4}$=9.5 Hz); 5.87 (dd, 1H, H2, $J_{H2\text{-}H1}$=8.0 Hz, $J_{H2\text{-}H3}$=9.5 Hz); 5.84 (t, 1H, H4, $J_{H4\text{-}H3}$=$J_{H4\text{-}H5}$=9.6 Hz); 4.66 (dd, 1H, H6, $J_{H6\text{-}H5}$=2.9 Hz, $J_{H6\text{-}H6'}$=12.3 Hz); 4.52 (dd, 1H, H6', $J_{H6'\text{-}H5}$=4.7 Hz, $J_{H6'\text{-}H6}$=12.3 Hz); 4.41 (ddd, 1H, H5, $J_{H5\text{-}H4}$=9.7 Hz, $J_{H5\text{-}H6}$=3.0 Hz, $J_{H5\text{-}H6'}$=4.6 Hz); α anomer: 6.85 (d, 1H, H1, $J_{H1\text{-}H2}$=3.8 Hz); 6.33 (t, 1H, H3, $J_{H3\text{-}H2}$=$J_{H3\text{-}H4}$=10.0 Hz); 5.88 (t, 1H, H4, $J_{H4\text{-}H3}$=$J_{H4\text{-}H5}$=9.8 Hz); 5.69 (dd, 1H, H2, $J_{H2\text{-}H1}$=3.8 Hz, $J_{H2\text{-}H3}$=10.3 Hz); 4.65–4.60 (m, 2H, H5, H6); 4.48 (dd, 1H, H6', $J_{H6'\text{-}H5}$=5.0 Hz, $J_{H6'\text{-}H6}$=13.0 Hz).

b) Preparation of ethyl 2,3,4,6-tetra-O-benzoyl-1-thio-D-glucopyranoside

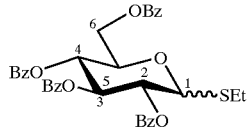

100 g of perbenzoyl glucose (143 mmol; 1 eq) are dissolved in 2 l of dichloromethane and the reaction medium is brought to reflux and 12.7 ml of ethanethiol (171 mmol; 1.2 eq) and 54.2 ml (429 mmol; 3 eq) of boron trifluoride etherate are added thereto. After 2 hours of reaction in total, the medium is diluted with dichloromethane, washed with a 5% solution of sodium hydrogen carbonate and then with water until pH neutral. The product is recrystallised from ethyl acetate and 73 grams of product are thus collected.

Yield (%): 80

White solid.

M. Pt. (°C.)=133–134 (α anomer)

TLC: R$_f$=0.4 (β anomer); 0.5 (α anomer)(petroleum ether/ethyl acetate (8/2; v/v)).

$^{13}$C NMR (CDCl$_3$, 101 MHz) δ(ppm): 166.23, 166.18, 165.87, 165.71, 165.50, 165.38, 165.27 (C=O); α anomer: 82.10 (C1); 71.74 (C2); 70.99 (C3); 69.62 (C4); 68.21 (C5); 63.14 (C6); 24.34 (CH$_2$); 14.71 (CH$_3$); β anomer: 84.02 (C1); 76.37 (C5); 74.19 (C3); 70.68 (C2); 69.71 (C4); 63.42 (C6); 24.47 (CH$_2$); 15.01 (CH$_3$).

$^1$H NMR (CDCl$_3$, 400 MHz) δ(ppm): 8.06–7.26 (2m, 40H, H arom.); α anomer: 6.08 (t, 1H, H3, $J_{H3\text{-}H2}$=$J_{H3\text{-}H4}$=9.9 Hz); 5.95 (d, 1H, H1, $J_{H1\text{-}H2}$=5.8 Hz); 5.68 (t, 1H, H4, $J_{H4\text{-}H3}$=$J_{H4\text{-}H5}$=9.9 Hz); 5.51 (dd, 1H, H2, $J_{H2\text{-}H1}$=5.8 Hz, $J_{H2\text{-}H3}$=10.2 Hz); 4.88 (ddd, 1H, H5, $J_{H5\text{-}H4}$=10.2 Hz, $J_{H5\text{-}H6}$=2.8 Hz, $J_{H5\text{-}H6'}$=5.4 Hz); 4.60 (dd, 1H, H6, $J_{H6\text{-}H5}$=2.8 Hz, $J_{H6\text{-}H6'}$=12.2 Hz); 4.52 (dd, 1H, H6', $J_{H6'\text{-}H5}$=5.4 Hz, $J_{H6'\text{-}H6}$=12.2 Hz); 2.62 (qd, 2H, CH$_2$, J=7.4 Hz, J=9.6 Hz); 1.25 (t, 3H, CH$_3$, J=7.4 Hz); β anomer: 5.93 (t, 1H, H3, $J_{H3\text{-}H2}$=$J_{H3\text{-}H4}$=9.7 Hz); 5.68 (t, 1H, H4, $J_{H4\text{-}H3}$=$J_{H4\text{-}H5}$=9.8 Hz); 5.57 (t, 1H, H2, $J_{H2\text{-}H1}$=$J_{H2\text{-}H3}$=9.7 Hz); 4.87 (d, 1H, H1, $J_{H1\text{-}H2}$=10 Hz); 4.64 (dd, 1H, H6, $J_{H6\text{-}H5}$=3.1 Hz, $J_{H6\text{-}H6'}$=12.1 Hz); 4.50 (dd, 1H, H6', $J_{H6'\text{-}H5}$=5.5 Hz, $J_{H6'\text{-}H6}$=12.1 Hz); 4.18 (ddd 1H, H5, $J_{H5\text{-}H4}$=10.0 Hz, $J_{H5\text{-}H6}$=3.0 Hz, $J_{H5\text{-}H6'}$=5.5 Hz); 2.77 (qd, 2H, CH$_2$, J=7.4 Hz, J=9.6 Hz); 1.26 (t, 3H, CH$_3$, J=7.4 Hz).

EXAMPLE 3

Example of a Coupling Reaction According to the Invention

A coupling reaction between the donor of Example 2 and the acceptor of Example 1 was carried out to give the following novel compound:

2,3,4,6-tetra-O-benzoyl-β-D-glucopyranosyl-(1→3)-1.2:5,6-di-O-cyclohexylidene-α-D-glucofuranose

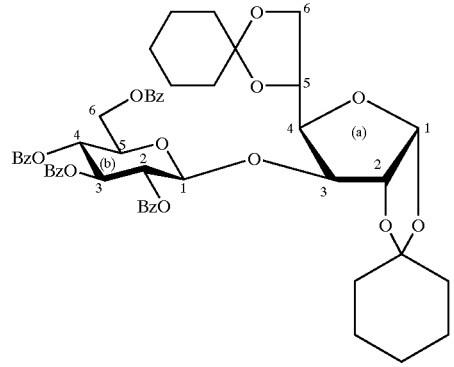

64 g (100 mmol; 1.06 eq) of ethyl 2,3,4,6-tetra-O benzoyl-1-thio-D-glucopyranoside, 32 g (94 mmol; 1 eq) of 1,2:5,6-di-O-cyclohexylidene-α-D-glucofuranose, 22.5 g (100 mmol; 1.06 eq) of N-iodosuccinimide and 400 g of 4 Å molecular sieves are introduced into a round-bottomed flask in the dark and then dissolved in 400 ml of anhydrous dichloromethane at a temperature of 10° C., and 3.92 grams (9.4 mmol; 0.1 eq) of tin ditriflate are then added. After 1 hour of reaction, the medium is neutralised with triethylamine, filtered and concentrated. Purification on a silica gel column (flash, eluent: toluene/ethyl acetate (95/5 then 9/1: v/v)) enables 60.5 grams of product to be collected.

Yield (%): 70

White solid.

TLC: R$_f$=0.4 (toluene/ethyl acetate (9/1; v/v)).

$^{13}$C NMR (CDCl$_3$, 101 MHz) δ(ppm): 166.19, 165.86, 165.20, 164.83 (C=O); 112.71, 109.32 (C quat.); 104.66 (C1a); 100.08 (C1b); 82.83 (C2a); 81.68 (C3a); 80.66 (C4a); 72.79 (C3b); 72.63 (C5b); 72.46 (C5a); 71.99 (C2b); 69.57 (C4b); 66.26 (C6a); 63.12 (C6b); 36.43, 36.33, 35.49, 34.61, 25.23, 24.84, 24.17, 23.89, 23.86, 23.54 (CH$_2$).

$^1$H NMR (CDCl$_3$, 400 MHz) δ(ppm): 8.03–7.26 (2m, 20H, H arom.); 5.90 (t, 1H, H3b, $J_{H3b\text{-}H2b}$=$J_{H3b\text{-}H4b}$=9.6 Hz); 5.71 (t, 1H, H4b, $J_{H4b\text{-}H3b}$=$J_{H4b\text{-}H5b}$=9.6 Hz); 5.52 (dd, 1H, H2b, JH2b-H1b=8.2 Hz, $J_{H2b\text{-}H3b}$=9.4 Hz); 5.45 (d, 1H, H1a, $J_{H1a\text{-}H2a}$=3.6 Hz); 4.99 (d, 1H, H1b, $J_{H1b\text{-}H2b}$=7.8 Hz); 4.64 (dd, 1H, H6b, $J_{H6b\text{-}H5b}$=2.4 Hz, $J_{H6\text{-}H6'b}$=12.2 Hz); 4.49 (dd, 1H, H6'b, $J_{H6'b\text{-}H5b}$=5.0 Hz, $J_{H6b\text{-}H6b}$=12.2 Hz); 4.38 (q, 1H, H5a, $J_{H5a\text{-}H4a}$=$J_{H5a\text{-}H6a}$=$J_{H5a\text{-}H6'a}$=6.1 Hz); 4.35 (d, 1H, H3a, $J_{H3a\text{-}H4a}$=3.0 Hz); 4.32 (d, 1H, H2a, $J_{H2a\text{-}H1a}$=3.6 Hz); 4.18 (dd, 1H, H4a, $J_{H4a\text{-}H3a}$=2.9 Hz, $J_{H4a\text{-}H5a}$=6.3 Hz); 4.11 (ddd, 1H, H5b, $J_{H5b\text{-}H4b}$=Hz, $J_{H5b\text{-}H6b}$=Hz, $J_{H5b\text{-}H6'b}$=Hz); 4,03 (dd, 1H, H6a, $J_{H6a\text{-}H5a}$=6.8 Hz, $J_{H6a\text{-}H6'a}$=8.3 Hz); 3.94 (dd, 1H, H6'a, $J_{H6'a\text{-}H5a}$=5.6 Hz, $J_{H6'a\text{-}H6a}$=8.3 Hz); 1.62–1.30 (m, 20H, CH$_2$).

EXAMPLE 4

Further Example of a Coupling Reaction According to the Invention

In this example, 2,3,4,6-tetra-O-benzoyl-β-D-glucopyranosyl-(1→3)-1,2:5,6-di-O-isopropylidene-α-D-glucofuranose:

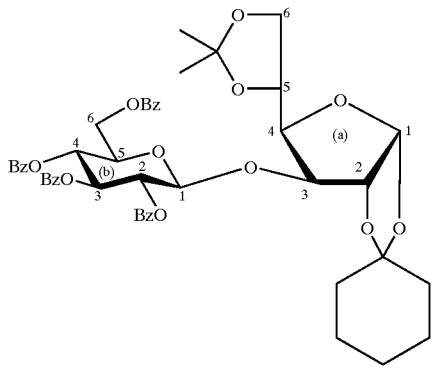

was prepared by a coupling reaction.

In this example, the glycosyl acceptor compound is diacetone D-glucose which can easily be obtained from D-glucose and acetone.

64 g (100 mmol; 1.06 eq) of ethyl 2,3,4,6-tetra-O-benzoyl-1-thio-D-glucopyranoside prepared in Example 2, 24.5 g (94 mmol; 1 eq) of diacetone-D-glucose, 22.5 g (100 mmol; 1.06 eq) of N-iodosuccinimide and 400 g of 4 Å molecular sieves are introduced into a round-bottomed flask in the dark and then dissolved in 400 ml of anhydrous dichloromethane. The reaction medium is cooled to 0° C. and 3.92 g (9.4 mmol; 0.1 eq) of tin ditriflate are added thereto. After 20 minutes of reaction, the medium is neutralised with triethylamine, filtered and concentrated. Purification on a silica gel column (flash, eluent:dichloromethane/ethyl acetate (95/5: v/v)) enables 28 grams of product to be collected.

Yield (%): 35

White solid.

M. Pt. (°C.)=90–94

TLC: $R_f$=0.5 (toluene/ethyl acetate (8/2; v/v)).

$^{13}$C NMR (CDCl$_3$, 101 MHz) δ(ppm): 166.16, 165.85, 165.19, 164.81 (C=O); 112.00, 108.72 (C quat.); 104.99 (C1a); 99.99 (C1b); 82.78 (C2a); 81.48 (C3a); 80.47 (C4a); 73.05 (C5a); 72.72 (C3b); 72.65 (C5b); 71.85 (C2b); 69.54 (C4b); 66.25 (C6a); 62.98 (C6b); 26.73, 26.67, 26.03, 25.15 (CH$_3$).

$^1$H NMR (CDCl$_3$, 400 MHz) δ(ppm): 8.03–7.26 (2m, 20H, H arom.); 5.90 (t, 1H, H3b, $J_{H3b-H2b}$=$J_{H3b-H4b}$=9.7 Hz); 5.71 (t, 1H, H4b, $J_{H4b-H3b}$=$J_{H4b-H5b}$=9.7 Hz); 5.50 (dd, 1H, H2b, $J_{H2b-H1b}$=7.8 Hz, $J_{H2b-H3b}$=9.7 Hz); 5.48 (d, 1H, H1a, $J_{H1a-H2a}$=3.7 Hz); 4.98 (d, 1H, H1b, $J_{H1b-H2b}$=7.8 Hz); 4.66 (dd, 1H, H6b, $J_{H6b-H5b}$=3.2 Hz, $J_{H6b-H6'b}$=12.2 Hz); 4.50 (dd, 1H, H6'b, $J_{H6'b-H5b}$=5.1 Hz, $J_{H6'b-H6b}$=12.2 Hz); 4.38 (m, 1H, H5a); 4.34 (d, 1H, H2a, $J_{H2a-H1a}$=3.7 Hz); 4.33 (d, 1H, H3a, $J_{H3a-H4a}$=3.2 Hz); 4.23 (dd, 1H, H4a, $J_{H4a-H3a}$=3.2 Hz, $J_{H4a-H5a}$=5.5 Hz); 4.16 (ddd, 1H, H5b, $J_{H5b-H4b}$=9.7 Hz, $J_{H5b-H6b}$=3.2 Hz, $J_{H5b-H6'b}$=5.1 Hz); 4.04 (dd, 1H, H6a, $J_{H6a-H5a}$=6.5 Hz, $J_{H6a-H6'a}$=8.6 Hz); 3.97 (dd, 1H, H6'a, $J_{H6'a-H5a}$=5.7 Hz, $J_{H6'a-H6a}$=8.6 Hz); 1.42, 1.37, 1.25, 1.12 (4s, 12H, CH$_3$).

EXAMPLE 5

This Example Illustrates a Deprotection Reaction which Gives Laminaribiose and which is Carried Out in Two Steps According to the Invention a) 2,3,4,6-tetra-O-benzoyl-β-D-glucopyranosyl-(1→3)-D-glucopyranose

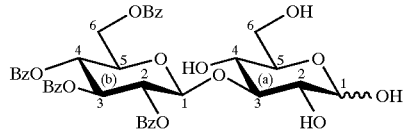

82 g of 2,3,4,6-tetra-O-benzoyl-β-D-glucopyranosyl-(1→3)-1,2:5,6-di-O-cyclohexylidene-α-D-glucofuranose prepared in Example 3 are dissolved in 600 ml of a mixture of equal volumes of trifluoroacetic acid and water to which 60 ml of tetrahydrofuran are added in order to obtain a good dissolution of the product in the reaction medium. After 1 day of reaction, at 40° C., the product is precipitated out by diluting the reaction medium with water, filtered, rinsed with water to neutrality, dried and purified by crystallisation in methanol. 54 g of the desired product were thus obtained.

Yield (%): 80

White solid.

M.Pt. (°C.)=183–186; 197–200 (2 α and β anomers).

TLC: $R_f$=0.6 (dichloromethane/methanol (9/1; v/v)).

$^{13}$C NMR (pyr. d$^5$, 101 MHz) δ(ppm): 165.90, 165.87, 165.81, 165.65, 165.58, 165.39, 165.37 (C=O); 133.41, 133.22, 133.00, 132.96, 132.93 (C ipso arom.); 130.05–128.28 (C arom.); 101.89, 101.70 (C1b); 98.46 (C1aβ); 93.59 (C1aα); 86.48 (C3aβ); 84.69 (C3aα); 77.78 (C5aβ); 75.80 (C2aβ); 74.09, 74.06 (C3b); 73.24 (C2aα); 73.04, 72.95, 72.90 (C5aα, C2b); 72.04 (C5b); 70.36, 70.29 (C4b); 69.55, 65.45 (C4a); 63.34, 63.24 (C6b); 62.51, 62.36 (C6a).

$^1$H NMR (pyr. d$^5$, 400 MHz) δ(ppm): 8.29–7.09 (3m, 40H, H arom.); 6.58 (t, 1H, H3b, $J_{H3b-H4b}$=$J_{H3b-H2b}$=9.5 Hz); 6.52 (t, 1H, H3b, $J_{H3b-H4b}$=$J_{H3b-H2b}$=9.5 Hz); 6.32 (d, 1H, H1b, $J_{H1b-H2b}$=8.0 Hz); 6.23–6.10 (m, 5H, 2 H4b, H1b, 2 H2b); 5.69 (d, 1H, H1aα, $J_{H1aα-H2aα}$=3.4 Hz); 5.22 (d, 1H, H1aβ, $J_{H1aβ-H2aβ}$=7.4 Hz); 4.94 (dd, 1H, H6b, $J_{H6b-H5b}$=2.7 Hz, $J_{H6b-H6'b}$=12.1 Hz); 4.88–4.69 (m, 6H, H6b, H3aα, H6b, H5aα, H6b, H5b); 4.52–4.57 (m, 3H, H6aα, H6aβ, H5b); 4.45 (t, 1H, H3aβ, $J_{H3aβ-H4aβ}$=$J_{H3aβ-H2aβ}$=9.1 Hz); 4.34–4.26 (m, 2H, H6'aα, H6'aβ); 4.20–4.13 (m, 2H, H4aα, H4aβ); 4.10–4.03 (m, 2H, H2aα, H2aβ); 3.97–3.93 (ddd, 1H, H5aβ).

b) Obtaining Laminaribiose

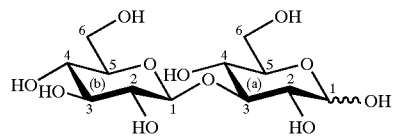

40 g (52.7 mmol; 1 eq) of 2,3,4,6-tetra-O-benzoyl-β-D-glucopyranosyl-(1→3)-D-glucopyranose are treated with 1 l of a solution of sodium methoxide (0.1 eq of sodium) prepared beforehand by dissolving 6 g of sodium in 40 l of anhydrous methanol. After 4 days of reaction at 35° C., the medium is diluted with water and then neutralised with acidic resin IR 120, filtered and concentrated. After lyophilisation, 18 g of laminaribiose are collected. The product can be crystallised in a methanol-water or ethanol-water mixture.

Yield(%): 100
White solid.
M. Pt. (°C.)=199–204 (ethanol-water; Bächli, Percival, *J. Chem. Soc.*, 1952, 1243: 196–206; Takeo, *Carbohydr. Res.*, 1979, 77, 245: 202–204).
M. Pt. (°C.)=124–130 (lyophilised laminaribiose).
$[\alpha]_D^{20}$=+19.3° (20 min)→+18.7°(24 h; c=1.0; water) (Takeo, *Carbohydr. Res.*, 1979, 77, 245: $[\alpha]_D^{20}$=+15.5° (10 min)→+18.6° (24 h; c=2.3; water)).
TLC: $R_f$=0.1 (ethyl acetate/isopropanol/methanol/water (10/6/1/1; v/v).
$^{13}$C NMR (DMSO d$^6$, 101 MHz) δ(ppm): β anomer: 104.16 (C1b); 96.33 (C1a); 88.43 (C3a); α anomer: 104.04 (C1b); 91.78 (C1a); 85.19 (C3a); 76.93, 76.87, 76.24, 76.10, 76.07, 73.87, 73.84, 73.50, 71.90, 70.90, 70.18, 70.13, 68.66, 68.57, 61.10, 60.92.
$^1$H NMR (D$_2$O, 400 MHz) δ(ppm): 5.11 (d, 1H, H1aα, $J_{H1a\alpha-H2a\alpha}$=3.8 Hz); 4.61 (d, 1H, H1b, $J_{H1b-H2b}$=7.9 Hz); 4.60 (d, 1H, H1b, $J_{H1b-H2b}$=7.6 Hz); 4.55 (d, 1H, H1b, $J_{H1a\beta-H2a\beta}$=8.0 Hz); 3.81–3.57 (m, 12H); 3.42–3.22 (m, 12H).

EXAMPLE 6
Characterisation of Laminaribiose

In order to characterise the product obtained, the laminaribiose synthesised was acetylated in the presence of acetic anhydride (12 eq) in pyridine and then recrystallised from ethanol. The β anomer, i.e. 1,2, 2', 3', 4, 4', 6, 6'-octa-O-acetyl-β-D-glucopyranose:

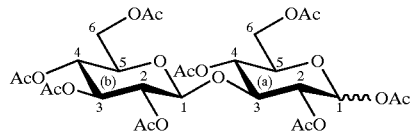

was obtained exclusively.
Yield (%): 100
White solid.
M. Pt. (°C.)=165–167 (Takeo, *Carbohydr. Res.*, 1979, 77, 245: 161–162).
$[\alpha]_D^{20}$=−27° (c=1.0; chloroform) (Takeo, *Carbohydr. Res.*, 1979, 77, 245: $[\alpha]_D^{20}$=−27.6° (c=1.2; chloroform)).
TLC: $R_f$=0.3 (toluene/ethyl acetate (1/1; v/v)).
$^{13}$C NMR (CDCl$_3$, 101 MHz) δ(ppm): 170.79, 170.57, 170.45, 169.38, 169.37, 169.29, 169.20, 168.92 (C=O); 101.02 (C1b); 91.80 (C1a); 78.92 (C3a); 72.98, 72.87 (C5a, C3b or vice versa); 71.15 (C2b); 67.99 (C4b); 67.56 (C4a); 61.73, 61.71 (C6a, C6b or vice versa); 20.91, 20.88, 20.84, 20.74, 20.64, 20.62, 20.52, 20.39 (CH$_3$).
$^1$H NMR (CDCl$_3$, 400 MHz) δ(ppm): 5.61 (d, 1H, H1a, $J_{H1a-H2a}$=8.4 Hz); 5.13 (t, 1H, H3b, $J_{H3b-H2b}$=$J_{H3b-H4b}$=9.4 Hz); 5.12 (dd, 1H, H2a, $J_{H2a-H1a}$=8.4 Hz, $J_{H2a-H3a}$=9.5 Hz); 5.06 (t, 1H, H4b, $J_{H4b-H3b}$=$J_{H4b-H5b}$=9.6 Hz); 5.01 (t, 1H, H4a, $J_{H4a-H3a}$=$J_{H4a-H5a}$=9.6 Hz); 4.90 (dd, 1H, H2b, $J_{H2b-H1b}$=8.1 Hz, $J_{H2b-H3b}$=9.3 Hz); 4.59 (d, 1H, H1b, $J_{H1b-H2b}$=8.1 Hz); 4.37 (dd, 1H, H6a, $J_{H6a-H5a}$=4.3 Hz, $J_{H6a-H6'a}$=12.4 Hz); 4.21 (dd, 1H, H6b, $J_{H6b-H5b}$=4.6 Hz, $J_{H6b-H6'b}$=12.4 Hz); 4.13 (dd, 1H, H6'b, $J_{H6'b-H5b}$=2.2 Hz, $J_{H6'b-H6b}$=12.4 Hz); 4.05 (dd, 1H, H6'a, $J_{H6'a-H5a}$=2.2 Hz, $J_{H6'a-H6a}$=12.4 Hz); 3.93 (t, 1H, H3a, $J_{H3a-H2a}$=$J_{H3a-H4a}$=9.4 Hz); 3.78 (ddd, 1H, H5a, $J_{H5a-H4a}$=10.1 Hz, $J_{H5a-H6a}$=2.2 Hz, $J_{H5a-H6'a}$=4.6 Hz); 3.68 (ddd, 1H, H5b, $J_{H5b-H4b}$=9.9 Hz, $J_{H5b-H6b}$=4.3 Hz, $J_{H5b-H6b}$=4.3 Hz, $J_{H5b-H6'b}$=2.3 Hz); 2.12, 2.09, 2.08, 2.03, 2.00, 1.98 (6s, 24H, CH$_3$).

What is claimed is:
1. A method of preparing laminaribiose comprising a step of glycosidic coupling between a glycosyl donor and a glycosyl acceptor, wherein:
the glycosyl donor is in pyranose form and is of formula (II):

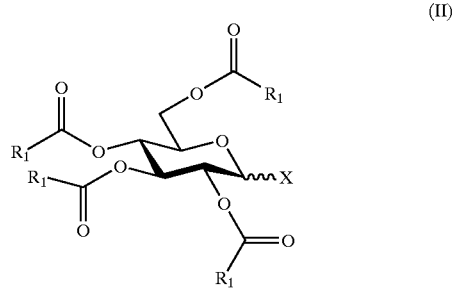

in which:
R$_1$ represents:
an alkyl or haloalkyl radical having 1 to 6 carbon atoms;
an aryl radical which is non-substituted or substituted with one or more groups selected from the group consisting of a halogen atom, an alkoxy radical having 1 to 6 carbon atoms and a nitro group;
X represents an electrophilic leaving group selected from the group consisting of:
a group of formula S(O)$_n$R' in which R' represents a radical selected from the group consisting of an alkyl radical having 1 to 6 carbon atoms, an aryl radical which is non-substituted or substituted with an alkoxy group having 1 to 6 carbon atoms, a nitro and acetamide group, and n is an integer equal to 0 or 1 and;
a trichloroacetimidate group;
the glycosyl acceptor is in furanose form and is of formula (III)

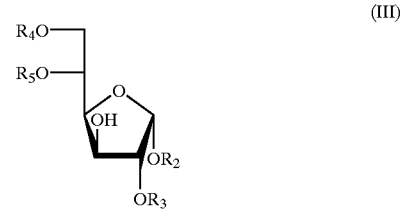

in which:
R$_2$ and R$_3$ together form a radical selected from the group consisting of a methylidyl, ethylidyl, trichloroethylidyl, isopropylidyl, hexafluoroisopropylidyl, cyclopentylidyl, cyclohexylidyl, cycloheptylidyl, butylidyl, 1-tert-butylethylidyl, 1-phenylethylidyl, benzylidyl, methoxybenzylidyl, and 1-phenylbenzylidyl radical; and
R$_4$ and R$_5$ together form a radical selected from the group consisting of a methylidyl, ethylidyl, trichloroethylidyl, isopropylidyl, hexafluoroisopropylidyl, cyclopentylidyl, cyclohexylidyl, cycloheptylidyl, butylidyl, 1-tert-butylethylidyl, 1-phenylethylidyl, benzylidyl, methoxybenzylidyl, or 1-phenylbenzylidyl radical;

or independently represent a benzyl, acetyl, benzoyl chlorobenzoyl, methoxybenzoyl, nitrobenzoyl, allyl, chlorobenzyl, methoxybenzyl and nitrobenzyl radical;

said coupling step is carried out in solution in an anhydrous organic solvent, at a temperature between −80° C. and 40° C., for a period of 1 minute to 8 hours, in the presence of a suitable promoter selected from the group consisting of:

N-bromosuccinimide or N-iodosuccinimide, combined with a Lewis acid selected from the group consisting of ferric chloride, copper ditriflate, tin ditriflate, boron trifluoride dietherate, tin or zirconium tetrachloride, methyl triflate, trimethyl- (or triethyl-) silyl triflate, silver triflate, cadmium ditriflate, cobalt ditriflate, nickel ditriflate, zinc ditriflate, bismuth tritriflate, iron tritriflate, and gallium tritriflate, in the case in which X represents an $S(O)_nR'$ group as defined above in which n is equal to 0, a Lewis acid selected from the group consisitng of triflic anhydride, ferric chloride, copper ditriflate, tin ditriflate, boron trifluoride dietherate, tin or zirconium tetrachloride, methyl triflate, trimethyl- (or triethyl-) silyl triflate, silver triflate, cadmium ditriflate, cobalt ditriflate, nickel ditriflate, zinc ditriflate, bismuth tritriflate, iron tritriflate, and gallium tritriflate, combined with an amine, in the case in which X represents an $S(O)_nR'$ group as defined above in which n is equal to 1, and a Bronsted acid or a Lewis acid selected from the group consisting of triflic anhydride, ferric chloride, copper ditriflate, tin ditriflate, boron trifluoride dietherate, tin or zirconium tetrachloride, methyl triflate, trimethyl- (or triethyl-) silyl triflate, silver triflate, cadmium ditriflate, cobalt ditriflate, nickel ditriflate, zinc ditriflate, bismuth tritriflate, iron tritriflate, and gallium tritriflate, in the case in which X represents a trichloroacetimidate group; and the reaction product thus obtained, neutralised and purified, being subjected to a deprotection treatment to give, after purification, laminaribiose.

2. The method according to claim 1, wherein:

the glycosyl donor is of formula (II) mentioned above in which:

R1 represents a radical selected from the group consisting of methyl, chloromethyl, trifluoromethyl, tert-butyl, phenyl, chlorophenyl, methoxyphenyl and nitrophenyl radicals; and X represents a radical selected from the group consisting of thiomethyl, thioethyl, thiopropyl, thiophenyl, thionitrophenyl and thiopyridyl radicals.

3. The method according to claim 2 wherein:

the glycosyl donor is of formula (II) mentioned above in which:

$R_1$ represents a phenyl radical; and

X represents an $S(O)_nR'$ radical in which n is equal to 0 and R' represents an ethyl or phenyl radical;

the glycosyl acceptor is of formula (III) mentioned above in which:

$R_2$, $R_3$ and $R_4$, $R_5$ together form a cyclohexylidyl or isopropylidyl radical.

4. The method according to claim 3, wherein:

the promoter mentioned above is a mixture of N-iodosuccinimide and of tin ditriflate.

5. The method according to claim 3, wherein:

the promoter mentioned above is a mixture of N-iodosuccinimide and of tin ditriflate, in proportions between 1:0.5 and 1:0.005.

6. The method according to claim 1 wherein the deprotection treatment mentioned above comprises:

a) cleaving the acetal groups originating from the glycosyl acceptor by a treatment selected from the group consisting of an acidic treatment in an aqueous or hydro-organic medium, and a treatment in the presence of an acidic resin;

b) purifying the product thus obtained;

c) transesterifying or hydrolyzing the product obtained in step b); and d) purifying the product thus obtained.

7. The method according to claim 6, wherein said step a) mentioned above is carried out by allowing the neutralized and purified coupling product to react in a mixture of trifluoroacetic acid and water, at a temperature between 10 and 70° C. for a period of 1 hour to 10 days, and in that the purification step b) mentioned above is carried out by fractional crystallization.

8. The method according to claim 6, wherein said step a) mentioned above is carried out by allowing the neutralized and purified coupling product to react in a mixture of equal volumes of trifluoroacetic acid and water, at a temperature between 10 and 70° C. for a period of 1 hour to 10 days, and in that the purification step b) mentioned above is carried out by fractional crystallization in methanol.

9. The method according to claim 6, wherein the transesterification step mentioned above is carried out in an alcoholic solvent in the presence of a catalytic amount of an element selected from the group consisting of sodium, sodium methoxide, potassium methoxide, sodium ethoxide and potassium ethoxide for a period of 1 minute to 10 days, and in that the purification step d) mentioned above comprises:

d1) neutralizing the product obtained in step c), d2) removing the benzoic ester formed, either by azeotropic evaporation with water, or by extraction with an organic solvent, d3) concentrating under reduced pressure the residual aqueous phase.

10. The method according to claim 6, wherein the transesterification step mentioned above is carried out in an alcoholic solvent in the presence of a catalytic amount of an element selected from the group consisting of sodium, sodium methoxide, potassium methoxide, sodium ethoxide and potassium ethoxide for a period of 1 minute to 10 days, and in that the purification step d) mentioned above comprises:

d1) neutralizing the product obtained in step c), d2) removing the benzoic ester formed, either by azeotropic evaporation with water, or by extraction with an organic solvent, d3) concentrating under reduced pressure the residual aqueous phase, and d4) lyophilizing or crystallizing the laminaribiose thus obtained in a hydro-alcoholic mixture.

11. The method according to claim 1, wherein the coupling step mentioned above is carried out in solution in a solvent selected from the group consisting of dichloromethane, 1,2-dichloroethane and toluene, at a temperature between −30° C. and 30° C., for a period of 1 minute to 6 hours.

12. The method according to claim 1, wherein the coupling step mentioned above is carried out in solution in a solvent selected from the group consisting of dichloromethane, 1,2-dichloroethane and toluene, in the presence of molecular sieves, at a temperature between −30° C. and 30° C., for a period of 1 minute to 6 hours.

13. Laminaribiose synthesis intermediates, which are selected from the following compounds:

2,3,4,6-tetra-O-benzoyl-β-D-glucopyranosyl-(1→3)-1,2:5,6-di-O-cyclohexylidene-α-D-glucofuranose

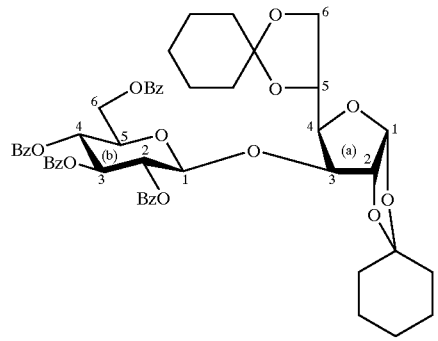

and 2,3,4,6-tetra-O-benzoyl-β-D-glucopyranosyl-(1→3)-D-glucopyranose:

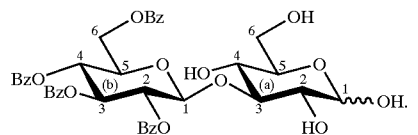

14. A method of preparing laminaribiose comprising a step of glycosidic coupling between a glycosyl donor and a glycosyl acceptor, wherein:

the glycosyl donor is in pyranose form and is of formula (II):

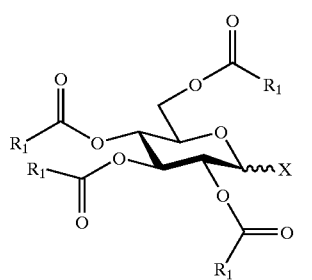

in which:

$R_1$ represents:
an alkyl or haloalkyl radical having 1 to 6 carbon atoms;

an aryl radical which is non-substituted or substituted with one or more groups selected from the group consisting of a halogen atom, an alkoxy radical having 1 to 6 carbon atoms and a nitro group;

X represents a trichloroacetimidate group;

a the glycosyl acceptor is in furanose form and is of formula (III)

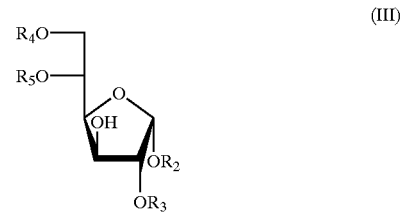

in which:

$R_2$ and $R_3$ together form a radical selected from the group consisting of a methylidyl, ethylidyl trichloroethylidyl, isopropylidyl, hexafluoroisopropylidyl, cyclopentylidyl, cyclohexylidyl, cycloheptylidyl, butylidyl, 1-tert-butylethylidyl, 1-phenylethylidyl, benzylidyl, methoxybenzylidyl, and 1-phenylbenzylidyl radical; and $R_4$ and $R_5$ together form a radical selected from the group consisting of a methylidyl, ethylidyl, trichloroethylidyl, isopropylidyl, hexafluoroisopropylidyl, cyclopentylidyl, cyclohexylidyl, cycloheptylidyl, butylidyl, 1-tert-butylethylidyl, 1-phenylethylidyl, benzylidyl, methoxybenzylidyl, or 1-phenylbenzylidyl radical, or independently represent a benzyl, acetyl, benzoyl, chlorobenzoyl, methoxybenzoyl, nitrobenzoyl, allyl, chlorobenzyl, methoxybenzyl and nitrobenzyl radical;

said coupling step is carried out in solution in an anhydrous organic solvent, at a temperature between −80° C. and 40° C., for a period of 1 minute to 8 hours, in the presence of a suitable promoter selected from the group consisting of a Bronsted acid or a Lewis acid selected from the group consisting of triflic anhydride, ferric chloride, copper ditriflate, tin ditriflate, boron trifluoride dietherate, tin or zirconium tetrachloride, methyl triflate, trimethyl- (or triethyl-) silyl triflate, silver triflate, cadmium ditriflate, cobalt ditriflate, nickel ditriflate, zinc ditriflate, bismuth tritriflate, iron tritriflate, and gallium tritriflate, in the case in which X represents a trichloroacetimidate group; and the reaction product thus obtained, neutralised and purified, being subjected to a deprotection treatment to give, after purification, laminaribiose.

* * * * *